United States Patent [19]

Becker et al.

[11] Patent Number: 5,015,755
[45] Date of Patent: May 14, 1991

[54] 9-ANTHRYLALKYL COMPOUNDS

[75] Inventors: Hans-Dieter Becker, Mölndal; Stefan Einarsson, Göteborg; Andrzej Grzegorczyk, Västra Frölunda; Björn Josefsson, Göteborg; Stig S. Lagerkvist, Göteborg; Per L. Möller, Göteborg; Domingo Sanchez, Floda; Johan H. Sörensen, Göteborg, all of Sweden

[73] Assignee: Eka Nobel AB, Surte, Sweden

[21] Appl. No.: 391,957

[22] Filed: Aug. 10, 1989

[30] Foreign Application Priority Data

Aug. 18, 1988 [SE] Sweden .................. 8802932

[51] Int. Cl.⁵ .................. C07C 69/96; C07D 207/416; C07D 255/02
[52] U.S. Cl. .................. 558/282; 548/528; 552/7
[58] Field of Search .................. 548/528; 552/7; 558/282

[56] References Cited

U.S. PATENT DOCUMENTS 3,211,752 10/1965 Breslow .................. 552/7
4,818,704 4/1989 Josefsson et al. .................. 558/282

FOREIGN PATENT DOCUMENTS

WO87/06929 11/1987 PCT Int'l Appl. .

OTHER PUBLICATIONS

*Journal of Chromatography*, "Determination of Amino Acids with 9-Fluorenylmethyl Chloroformate and Reversed-Phase High-Performance Liquid Chromatograph", 282, (1983), pp. 609–618.
*Journal of Organic Chemistry*, "Synthesis and Photochemical Isomerization of 1,2-Di-9-Anthrylethanol and 1,2-Di-9-Anthrylethanone", (1986), pp. 2956–2961.
*Journal of Organic Chemistry*, vol. 42, No. 2, (1977), pp. 399–400.
Beilstein E III, vol. 6 (1967), p. 3573.

*Primary Examiner*—Richard L. Raymond
*Attorney, Agent, or Firm*—Burns, Doane, Swecker & Mathis

[57] ABSTRACT

New 9-anthrylalkyl compounds having the general formula

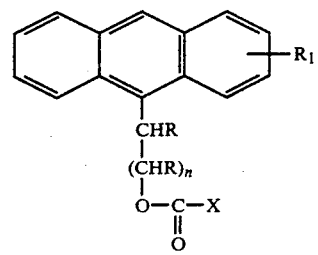

wherein R is hydrogen or an alkyl group, whereby, however, not more than one of the groups R is an alkyl group; $R_1$ is hydrogen, lower alkyl, halogen or nitro; n is an integer of from 1 to 7, whereby, however, the total number of carbon atoms in the group —CHR—(CHR-)$_n$— does not exceed 8; and X is halogen, an azide group or a succinimidyl group.

The new compounds are prepared from 9-anthrylalcohols which are reacted with a compound X—CO—X wherein X is a halogen, and then optionally with compounds giving azide or succinimidyl group. The compounds are used as derivatization reagents for separation and detection purposes.

Intermediates for preparation of the above defined 9-anthrylalkyl compounds wherein one R is an alkyl group are 9-anthrylalcohols with the group —CHR—(CHR)$_n$—OH, wherein one R is an alkyl group.

10 Claims, No Drawings

9-ANTHRYLALKYL COMPOUNDS

The present invention relates to new compounds, which are certain 9-anthrylalkyl compounds. The invention also relates to the preparation of the compounds, to the use of the compounds as derivatization reagents for separation purposes and to certain intermediates for the preparation of the 9-anthrylalkyl compounds.

BACKGROUND

The preparation of derivatives of certain substances makes it possible to determine small amounts of these in complex samples such as blood plasma and urine. Chiral compounds can furthermore be resolved by formation of diastereomers with chiral reagents followed by separation using conventional HPLC-columns (high performance liquid chromatography) or GC-columns (gas chromatography).

Separation and determination of compounds such as amines, alcohols and amino acids and optical isomers of these has become more and more important because of their biochemical and pharmaceutical interest. A large number of reagents for derivatization of amines and amino acids for subsequent separation, for example by means of liquid chromatography, have been suggested but just a few have found any extensive use. Among the achiral reagents 9—fluorenylmethyl chloroformate (FMOC) has been developed during the last few years and found use for derivatization of amino acids. The amino acid derivatives are separated by HPLC and then determined by fluorescence detection, cf J. Chromatogr. 1983, pages 609–618 (S. Einarsson, B. Josefsson, S. Lagerkvist). Fluorescence detection with these reagents give detection at very low concentrations while UV-detection is limited to higher concentrations (low fmole respectively low pmole).

Among the chiral derivatization reagents, i.e. reagents which can be used also for separation of optical isomers, the reagent (+)-1-(9-fluorenyl)ethyl chloroformate (FLEC) has recently been developed and is disclosed in WO 87/06929. Also for this reagent the fluorescence detection is very good while the UV-detection is limited to higher concentrations.

The demands on and the desires for a reagent for separation purposes according to what has been discussed above are to a great extent the same for both achiral and chiral reagents. In addition to the fact that it of course should be possible to prepare them in a satisfactory manner, the reagents should form stable derivatives of the compounds to be determined and/or separated, in the first place with compounds containing amino groups, and hereby preferably both with primary and secondary such groups, but of course also with as many other types of compounds as possible for increased universality in use. The detection sensitivity should be as high as possible and it is highly desirable that more than one detection method can be used. It shall be possible to separate the prepared derivatives by conventional column separation. For chiral derivatization reagents it is also extremely important that it is possible that they can be prepared optically pure and that the derivatization can be carried out under mild conditions to avoid risk of racemization.

THE INVENTION

The present invention relates to new 9-anthrylalkyl compounds which are useful as derivatization reagents and which fulfill the demands on such agents. The compounds are particularly advantageous in that they allow detection by means of UV at very low concentrations (low fmole). The anthracene chromophore which is part of the compounds hereby gives the advantage that it is possible to utilize its absorption maxima (e.g. 256, 366 and 386 nm) for identification purposes. The new compounds according to the invention are 9-anthrylalkyl compounds and characterized by the general formula

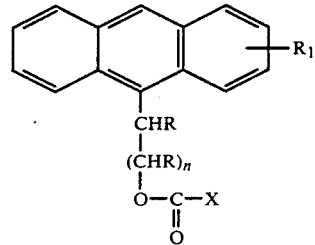

wherein R is hydrogen or an alkyl group, whereby, however, not more than one of the groups R is an alkyl group; $R_1$ is hydrogen, lower alkyl, halogen or nitro and is positioned arbitrarily in the anthracene ring; n is an integer of from 1 to 7, whereby, however, the total number of carbon atoms in the group —CHR-(CHR)$_n$- does not exceed 8; and X is halogen, an azide group or a succinimidyl group.

The compounds of the present invention are thus as well achiral as chiral compounds, where the latter thus contain an asymmetric carbon atom, i.e. R in the above given formula is an alkyl group. The chiral compounds can be in the form of a racemate or as the optically active isomers whereby the latter are prepared from the intermediate alcohol racemate by per se conventional resolution methods, for example as disclosed in the examples. Compounds wherein the total number of carbon atoms in the group —CHR-(CHR)$_n$- does not exceed 4 are preferred since these are the most stable substances and have the best separation capability. It is particularly preferred that the group does not contain more than 3 carbon atoms. For the chiral compounds it is further preferred that these are such wherein the β-carbon, counted from the anthryl nucleus, is asymmetric. Optional $R_1$ substituents are the above defined groups which are electron attracting groups. If $R_1$ is a lower alkyl group it should suitably have from 1 to 5 carbon atoms and preferably be a methyl or ethyl group. The group X shall be a group which is easily split off at reaction with the compounds in question and X can hereby be a halogen, such as chlorine or bromine, and the mentioned azide- and succinimidyl groups, which have been found to be satisfactory such groups. It is particularly preferred that X is a halogen, suitably chlorine or bromine, and especially chlorine, i.e. that the compounds are 9-anthrylalkyl chloroformates. Particularly preferred compounds are the achiral compound 2-(9-anthryl)ethyl chloroformate (AEOC) and the chiral compounds (+)-1-(9-anthryl)-2-propyl chloroformate and (−)-1-(9-anthryl)-2-propyl chloroformate The invention further relates to preparation of the new compounds according to the features given in the patent claims. The compounds can be prepared starting from the corresponding 9-anthrylalcohol which gives the desired group —CHR-(CHR)$_n$-, whereby the alcohol is reacted with a compound which provides the group —C(O)-X. The 9-anthrylalcohol as such can be prepared for example from 9-bromoanthracene via 9-anthryllithium by reaction with an alkyleneoxide, cf J. Org. Chem., 1986, 51, 2956-2961. For preparation of chloroformate the reaction is suitably carried out by reacting the 9-anthrylalcohol in question with phosgene. To obtain compounds wherein X is bromine the 9-anthrylalcohol is suitably reacted with Br-phosgene. To obtain compounds wherein X is an azide group or a succinimidyl group the respective haloformate is suitably reacted with sodium azide and, respectively, N-hydroxysuccinimide-dicyclohexyl ammonium salt. The reaction between the anthrylalcohol and the reagent which provides the group —C(O)-X is normally carried out in an inert solvent, such as for example toluene, and suitably in the presence of a base, e.g. pyridine. The reaction can be carried out at temperatures of from 0° C. to 110° C. Stoichiometric amounts of anthrylalcohol and reagent can be used. Normally the reaction times are from 0.5 to 3 hours.

At preparation of chloroformates the anthrylalcohol is suitably reacted with phosgene in a solvent such as methylene chloride or toluene, whereby the reaction is carried out at temperatures of from 0° C. to room temperature.

The invention also relates to the use of the compounds according to the invention. The compounds are particularly suitable as derivatization reagents for separation and detection purposes. They react with primary, secondary and/or tertiary amino groups in aqueous and nonaqueous solutions at room temperature. The reaction is very rapid and stable carbamates are obtained. In corresponding manner as the compounds of the invention react with amino groups, and thus with compounds such as amines and amino acids, they also react with compounds containing hydroxyl groups and form stable carbonates. Alcohols and carbohydrates can thus also be derivatized and be detected with the present reagents. For complete derivatization it is suitable to use a comparatively large excess of the reagent, at least an excess of up to 10 times. The reaction is selective and excess reagent can easily be extracted for example with pentane. The derivatization is rapid and high yields are obtained at room temperature. For amines the reaction is suitably carried out in buffered aqueous alkaline solutions.

The derivatized products can, as a rule after preceding separation, be detected at very low levels by as well UV-detection as fluorescence detection. A comparison with the corresponding derivatives of FMOC has shown a substantial improvement, i.e. a decrease, of the detection limits for both UV-detection and fluorescence detection by derivatization with the present compounds. The actual separation can be carried out by means of conventional separation methods, such as different types of liquid chromatography, and is advantageously carried out by HPLC, which is the most efficient system for analysis of small amounts of substances and for preparative separation.

The chiral compounds according to the present invention give, in addition to the above disclosed separation and determination methods, also the possibility of separating optical isomers of for example amines, amino acids and alcohols. The chiral compounds give the same good detection properties as the achiral ones. The optically active forms of the reagents allow separation and quantitative determination of diastereomers of the derivatized products. The (−) isomers, e.g. (−)-anthrylpropyl chloroformate, form together with amino acids a diastereomeric pair, where the D-form is separated before the L-form, which is advantageous since the L-form is the dominating form in most samples.

The invention also relates to intermediate anthrylalcohols for preparation of the above defined new chiral compounds, and these intermediates have the general formula

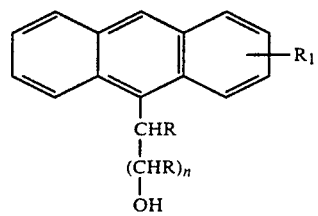

wherein R is an alkyl group and the others are hydrogen; R$_1$ is hydrogen, lower alkyl, halogen or nitro and is positioned arbitrarily in the anthracene ring; and n is an integer of 1 to 7, whereby, however, the total number of carbon atoms in the group —CHR-(CHR)n- does not exceed 8.

The suitable and preferred definitions for the intermediate anthrylalcohols are as specified above for the reagent compounds. The intermediates can for example be prepared by subjecting a 9-anthrylalkyl aldehyde to a Grignard reaction with CH$_3$MgI. Another method of preparation is reaction between 9-anthryllithium and an epoxialkane.

The new derivatization reagents, and especially 2-(9-anthryl)ethyl chloroformate (AEOC) and (+) and (−) 1-(9-anthryl)-2-propyl chloroformate, are particulary useful for quantitative determination of amino acids, amines and compounds containing hydroxyl groups, and their optical isomers, by reversed phase LC (reversed phase liquid chromatography). The reagents react with amino groups and hydroxyl groups in aqueous solutions during a couple of minutes at room temperature and stable carbamates and carbonates, respectively, are formed. The reaction is selective and excess reagent can be extracted with pentane. The detection of the derivatized products is favoured by the electron spectral properties of the anthracene chromophore, light absorption value $\epsilon = 190.000$ M$^{-1}$·cm$^{-1}$ at around 256 nm. A comparison with 9-fluorenylmethyl chloroformate derivative (FMOC), light absorption value $\epsilon = 20.000$ M$^{-1}$·cm$^{-1}$, of amino acids show that the compounds according to the invention have about 10 times as great UV-sensitivity. The different absorption bands for anthracene (256, 366 and 386 nm) can be used to increase the selectivity at the detection. The large difference between excitation wave length and emission wave length of the compounds of the invention also improves the detection. Derivatives of amino acids and other mentioned compounds with the new reagents can be separated in 30 minutes using conventional reversed phase liquid chromatography with gradient elution.

EXAMPLE 1

Preparation of 1-(9-anthryl)-2-propanol (a) From 9-anthryllithium and 1,2-epoxipropane.

A solution of 1,2-epoxipropane (0.65 ml) in ether (20 ml) was added to an ice-cold solution of 9-anthryllithium, which had been prepared from 9-bromoanthracene (1.54 g; 6 mmoles) and n-butyllithium (3.75 g of a 1.6 M solution) in ether (50 ml). Work up after 35 minutes comprised addition of aqueous ammonium chloride, extraction of the aqueous layer with dichloromethane and flash chromatography on silica gel/dichloromethane. The thus obtained crystalline product was recrystallized from dichloromethane solution by addition of hexane. Three identical experiments gave 2.4 g (56%) of pale yellow needle shaped crystals, mp 105°–107° C.

(b) From 9-anthrylacetaldehyde by Grignard reaction.

9-anthrylacetaldehyde (1.1 g; 5 mmoles) was Soxhlet—extracted for a period of 6 hours in an ether solution (100 ml) of methylmagnesium iodide (30 mmoles; prepared from 0.72 g of magnesium). Work up as described above gave 1.05 g (89%) of 1-(9-anthryl)-2-propanol as pale yellow needle shaped crystals, mp 105°–107° C.

| Analysis: | | |
|---|---|---|
| Calculated for $C_{17}H_{16}O$: | C: 86.40; | H: 6.82 |
| Found: | C: 86.16; | H: 6.74 |

EXAMPLE 2

Resolution of 1-(9-anthryl)-2-propanol 1-(9-anthryl)-2-propanol (500 mg; 2.07 mmoles) were added to dry pyridine (25 ml) and then (−)-camphersulfonic acid chloride was added (2.28 mmoles; 493 mg; 10% excess). The solution was allowed to stand under agitation at room temperature for 1 hour. The pyridine solution was extracted with $CH_2Cl_2$+HCl (10%; 3 times) and $Na_2CO_3$ (5%; 2 times). The $CH_2Cl_2$-phase was evaporated to dryness which gave crystal formation. The crystals were precipitated in MeOH (90 ml) and this gave white crystals (700 mg); mp 169°–170° C. Theoretical yield: 874 mg.

The diastereomers were prepared on an HPLC-column (5×30 cm), 300 mg each time, and eluted with hexanol:ethylacetate=93:7; flow: 80 ml/min. The first isomer was obtained with 90% optical purity. The other isomer was obtained with 97% optical purity. The isomers were recrystallized separately in smallest possible amount of MeOH. 320 g of the first isomer (0.76 mmoles) were dissolved in THF (10 ml) and then $LiAlH_4$ (2×0.76 mmoles; 58 mg) were added. Work up in conventional manner with evaporation of the ether-phase gave 170 mg. Recrystallization in petroleum ether gave 125 mg; mp 122°–123° C.

320 mg of the other isomer were treated in the same manner as above, and the same results of analysis were obtained. Evaporation of the ether-phase to dryness gave 170 mg. Recrystallization in petroleum ether gave 116 mg; mp 122°–123° C. The racemic mixture has a melting point of 103° C.

EXAMPLE 3

Preparation of 1-(9-anthryl)-2-propyl chloroformate

Each isomer separately (95% optical purity; 125 and 116 mg respectively) was dissolved in dry toluene (50 ml). The solutions were ice-cooled and then $Et_3N$ (46 mg; 0.45 mmoles) and phosgene (122 mg; 1.23 mmoles) were added. The solutions were allowed to stand under stirring for 1 hour and were subsequently filtered. The toluene phase was evaporated to dryness and petroleum ether was added to the yellowish oil. The petroleum ether was filtered and evaporated and the NMR spectra did then show totally optically pure compounds with the below give rotation values.

Isomer I: $/\alpha/D^{25} = +44.0°$
Isomer II: $/\alpha/D^{25} = -44.5°$

EXAMPLE 4

Preparation of 9-anthrylethyl chloroformate

A solution in methylene chloride (20 ml) of 2-(9—anthryl)ethanol (3.5 g; 15.7 mmoles), which had been obtained by reaction between bromoanthracene and n-butyllithium and subsequent reaction with ethylene oxide was slowly added to an ice-cold solution of phosgene (20 ml; 38.4 mmoles; 20% in toluene). The reaction mixture was kept for 3 hours in an ice-bath and was then allowed to stand at room temperature during the night. Work up by vacuum evaporation of the solvent gave a crystalline residue, which was recrystallized from methylene chloride solution by precipitation with hexane to give 3.36 g (75%) of AEOC as practically colourless crystals, mp 85°–87° C. 270 MHz $^1$H-NMR in $CDCl_3$: 4.10 (t, J=8 Hz, 2 H); 4.66 (t, J=8 Hz, 2 H); 7.46–7.61 (m, 4 H); 8.03 (d, J=8 Hz, 2 H); 8.27 (d, J=8.6 Hz, 2 H); 8.43 (s, 1 H, H-10).

EXAMPLE 5

Preparation of 9-anthrylpropyl chloroformate

The preparation of 9-anthrylpropanol comprised reductive conversion of 9-anthrylpropionic acid. This is obtained either from 9-anthrylaldehyde by means of a Wittig-reaction and a subsequent catalytic hydrogenation step according to known technique, or from anthrone and acrylonitrile with subsequent reduction to acid. Reduction of the obtained 9-anthrylpropionic acid with $LiAlH_4$ gave 9-anthrylpropanol in a yield of 89%. The chloroformate of 9-anthrylpropanol ("APOC") was obtained in the same manner as disclosed above for "AEOC". It forms colourless crystals, mp 103°–106° C.

EXAMPLE 6

Derivatization of amino acids using 2-(9-anthryl)ethyl chloroformate (AEOC)

A borate buffer was prepared from 1 M boric acid solution which had been adjusted to a pH of 7.84 with sodium hydroxide. A 10 mM AEOC-solution in acetone and 1-propanol (volume ratio 1:2) was prepared daily using a 30 mM storage solution of AEOC in dried distilled acetone. A sample (400 μl) for derivatization, which is selected from amino acid standard solutions from Sigma (St. Louis, MO, USA), was mixed with borate buffer (100 μl; pH 7.84) which gave a desired pH of 8.55. A mixture of 500 μl of 10 mM reagent solution and 500 μl of buffered sample was allowed to react for 4 minutes and then followed by two extractions of the hydrolysis product with 2 ml of pentane to remove excess reagent. The derivatization was carried out in silane treated reaction vials of 3 ml.

The separation was carried out using a chromatography column (Spherisorb ODS2) and a liquid chromatograph (Varian, model 5000), and the amino acid derivatives were then detected by means of a UV-absorbance detector and a fluorescence detector. The phase separation of the amino acid sample was carried out using a three component solvent (A,B,C) by gradient elution. The mobile phase consisted of tetrahydrofuran (A), 50 mM sodiumacetate solution in a water-methanol mixture of 9:1 (C). The chromatography conditions were: flow 1.2 ml/min; room temperature.

EXAMPLE 7

Resolution of amino acids using (−)-1-(9-anthryl)-2-propyl chloroformate

Two amino acids, phenylalanine and proline, representing amino acids containing a primary and a secondary amino group respectively were chosen for the experiment. A standard containing the alcohol 1-(9-anthryl)-2-propanol, was used for confirmation of a formed byproduct by chromatography.

The separations were carried out using a Varian 5500 gradient delivery system. The samples were injected by means of a Rheodyne injection valve equipped with a 20 μl loop. The derivatives were detected with a Schoeffel model 970 fluorescence detector. The excitation wavelength was 250 nm. A cutoff filter was used on the emission side (370 nm).

Standards of the amino acids (Sigma), were diluted in 0.1 M borate-buffer (pH 8.5). The concentration of the amino acids in the borate buffer were as follows:
(a) L-phenylalanine 50 μM
(b) D-phenylalanine 50 μM
(c) L- and D-phenylalanine 50 μM (total)
(d) L- and D-proline 50 μM (total)
(e) L-proline 50 μM The buffered amino acids standards (500 μl) were reacted for 10 minutes at room temperature with equal volume of the reagent (5 mM, dissolved in acetone). The samples were subsequently extracted twice with approximately 1.5 ml of pentane and the pentane layers were discarded. After the extraction procedures part of the aqueous layer was injected on the column.

Separation conditions: Mobile phases: Tetrahydrofuran and an acetic acid buffer were used for the separations. The buffer was made of 3 ml glacial acetic acid in 1 l distilled water. The pH adjusted to 5.0 with concentrated sodium hydroxide. The separations were carried out in an isocratic mode: 45% THF/ 55% buffer for separation of D,L-phenylalanine, and 33% THF/ 67% buffer for separation of D,L-proline. Flow rate: 1 ml/min. The column used for the separations was a 25×0.46 cm column packed with 5-μm diameter particle size reversed phase material (TSK-GEL, Toyo Soda LTD).

The α-values for the D- and L-phenylalanine and the D- and L-proline separations were 1.11 and 1.19, respectively.

What is claimed is:

1. New 9-anthrylalkyl compounds comprising the general formula

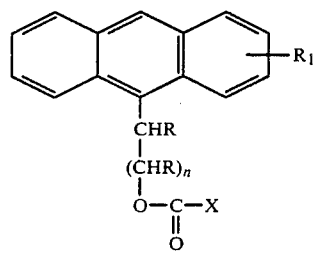

wherein R is hydrogen or an alkyl group, whereby, however, not more than one of the groups R is an alkyl group; $R_1$ is hydrogen, lower alkyl, halogen or nitro; n is an integer of from 1 to 7, whereby, however, the total number of carbon atoms in the group —CHR-(CHR)$_n$- does not exceed 8; and X is halogen, an azide group or a succinimidyl group.

2. Compounds according to claim 1, wherein the total number of carbon atoms in the group —CHR-(CHR)$_n$- does not exceed 4.

3. Compounds according to claim 1 wherein when R is an alkyl group it is positioned on the β-carbon atom, counted from the anthryl nucleus.

4. Compounds according to claim 1 wherein the total number of carbon atoms in the group —CHR-(CHR)$_n$- does not exceed 3.

5. Compounds according to claim 1 wherein X is chlorine.

6. Compound according to claim 1, wherein the compound is 2-(9-anthryl)ethyl chloroformate or 1-(9-anthryl)-2-propyl chloroformate.

7. Compound according to claim 6, wherein the compound is (−)-1-(9-anthryl)-2-propyl chloroformate or (+)-1-(9-anthryl)-2-propyl chloroformate.

8. Compounds according to claim 2, wherein X is chlorine.

9. Compounds according to claim 3, wherein X is chlorine.

10. Compounds according to claim 4, wherein X is chlorine.

* * * * *